(12) United States Patent
Bergersen

(10) Patent No.: US 10,980,615 B2
(45) Date of Patent: *Apr. 20, 2021

(54) ORAL APPLIANCE FOR ADVANCING THE MAXILLA AND OPENING THE NASOPHARYNGEAL AIRWAY

(71) Applicant: Ortho-Tain, Inc., Winnetka, IL (US)

(72) Inventor: Earl O. Bergersen, Dorado, PR (US)

(73) Assignee: Ortho-Tain, Inc., Dorado, PR (US)

( * ) Notice: Subject to any disclaimer, the term of this patent is extended or adjusted under 35 U.S.C. 154(b) by 147 days.

This patent is subject to a terminal disclaimer.

(21) Appl. No.: 15/666,878

(22) Filed: Aug. 2, 2017

(65) Prior Publication Data

US 2017/0325913 A1  Nov. 16, 2017

Related U.S. Application Data

(63) Continuation-in-part of application No. 15/343,907, filed on Nov. 4, 2016, now Pat. No. 10,537,407, which is a continuation of application No. 14/029,175, filed on Sep. 17, 2013, now Pat. No. 9,517,113.

(51) Int. Cl.
*A61C 7/08* (2006.01)
*A61C 7/10* (2006.01)
*A61C 7/36* (2006.01)
*A61F 5/56* (2006.01)

(52) U.S. Cl.
CPC .................. *A61C 7/36* (2013.01); *A61C 7/08* (2013.01); *A61F 5/566* (2013.01); *A61C 7/10* (2013.01)

(58) Field of Classification Search
CPC ... A61C 7/36; A61C 7/08; A61F 5/566; A61F 2005/563; Y10S 602/902
See application file for complete search history.

(56) References Cited

U.S. PATENT DOCUMENTS 3,478,742 A   11/1969  Bohlmann
4,139,944 A   2/1979   Bergersen
(Continued)

FOREIGN PATENT DOCUMENTS

FR    2867058 A1    9/2005
WO    9308761 A1    5/1993

*Primary Examiner* — Heidi M Eide
(74) *Attorney, Agent, or Firm* — Taft Stettinius & Hollister LLP

(57) ABSTRACT

An appliance for correcting a malocclusion in a mouth of a user, the appliance including a generally U-shaped upper body having an anterior portion configured to be adjacent to upper incisors and a posterior portion located rearward to the anterior portion, the upper body having an outer perimeter and an inner perimeter that is located interior to the outer perimeter; a generally U-shaped lower body having an outer perimeter, the outer perimeter of the lower body having an anterior portion adjacent to lower incisors and a posterior portion located rearward to the anterior portion of the lower body, wherein the lower body has a lower labial shield extending along the outer perimeter of the lower body; and lingual protrusions extending generally upward from the posterior portion of the inner perimeter of the upper body, the lingual protrusions being configured to contact a palate of the user as the appliance is worn within the mouth of the user.

13 Claims, 12 Drawing Sheets

(56) References Cited

U.S. PATENT DOCUMENTS

| | | | |
|---|---|---|---|
| 4,898,535 A * | 2/1990 | Bergersen | A61C 7/08 |
| | | | 433/6 |
| 5,592,951 A | 1/1997 | Castagnaro et al. | |
| 5,624,257 A * | 4/1997 | Farrell | A61C 7/08 |
| | | | 128/861 |
| 5,645,420 A | 7/1997 | Bergersen | |
| 5,682,903 A * | 11/1997 | Meade | A61F 5/566 |
| | | | 128/848 |
| 5,876,199 A | 3/1999 | Bergersen | |
| 7,234,933 B2 | 6/2007 | Bergersen | |
| 7,458,810 B2 | 12/2008 | Bergersen | |
| 7,716,062 B2 | 5/2010 | Bergersen | |
| 7,963,765 B2 | 6/2011 | Bergersen | |
| 7,975,701 B2 | 7/2011 | Bergersen | |
| 2003/0224312 A1 | 12/2003 | Bergersen | |
| 2003/0224313 A1 | 12/2003 | Bergersen | |
| 2004/0058295 A1 * | 3/2004 | Bergersen | A61C 7/08 |
| | | | 433/6 |
| 2004/0152032 A1 | 8/2004 | Bergersen | |
| 2006/0084024 A1 | 4/2006 | Farrell | |
| 2007/0240724 A1 | 10/2007 | Bergersen | |
| 2008/0178892 A1 * | 7/2008 | Haduong | A61F 5/566 |
| | | | 128/845 |
| 2010/0227289 A1 * | 9/2010 | Farrell | A61C 7/08 |
| | | | 433/6 |
| 2011/0264017 A1 * | 10/2011 | Smernoff | A61C 9/0006 |
| | | | 601/38 |
| 2012/0196243 A1 | 8/2012 | Farrell | |
| 2013/0244194 A1 | 9/2013 | Bergersen | |

\* cited by examiner

ORAL APPLIANCE FOR ADVANCING THE MAXILLA AND OPENING THE NASOPHARYNGEAL AIRWAY

CROSS-REFERENCE TO RELATED APPLICATIONS

This application is a continuation-in-part of U.S. patent application Ser. No. 15/343,907, which was filed on Nov. 4, 2016, and which in turn is a continuation of U.S. patent application Ser. No. 14/029,175, which was filed on Sep. 17, 2013, and was issued as U.S. Pat. No. 9,517,113 on Dec. 13, 2016. These applications are expressly incorporated in their entirety herein by this reference.

BACKGROUND OF THE INVENTION

The present invention relates to the correction of sleep-disordered breathing caused frequently by partial or complete reduction of the pharyngeal airway. Often mouth breathing allows the tongue to be displaced posteriorly and tends to partially or completely reduce the airway. Open mouth breathing while sleeping can be influenced by a reduction of nasal breathing capacity. Often this is due to excessive adenoid swelling, a naturally narrow nasopharynx or to the obstruction of the nasal airway. The expansion or widening of the maxilla can significantly improve nasal breathing capacity, which can also contribute to the correction of oropharyngeal reduction and mouth breathing.

There are other more invasive procedures to advance the maxilla. One such procedure is to place screws into the maxilla to enable an anterior force to reposition the upper jaw in a forward position with elastic or rubber band force. Another procedure is to cement brackets to the upper teeth and to place an exterior device called a reverse headgear onto the face that is attached to the maxillary appliance with elastic force. Other procedures often involve intraoral forces involving elastic rubber bands using the mandibular dentition as an anchorage unit to advance the maxilla or maxillary dentition. This procedure is termed Class III elastic force.

If it is determined that the reduced airflow through the nasal airway is due to nasal obstruction, surgical alteration of swollen turbinates, a deviated septum or polyps is often recommended. A plastic device that can be preformed and designed to utilize forces within the oral cavity by using the force of the tongue in a forward direction to advance the maxilla is an easy and simple solution to nasopharyngeal restriction. In a similar way, advancement of the mandible can prevent closure of the oropharyngeal airway all with the same oral appliance.

Typically, a diagnosis of a narrow nasopharyngeal or velopharyngeal airway is made by a lateral cephalometric radiograph where the pharynx can be measured regarding its width or square area. As stated previously, nasopharyngeal restriction can be due to adenoid tissue swelling or a thickened and large uvula. However, the airway may be naturally narrow and in such cases, can be corrected by moving the maxilla in an anterior direction.

By using the force of the tongue, it is not necessary to create this force by using other teeth, such as the lower dentition, as anchorage to counteract the elastic force against the maxilla. Another technique to open the airway by moving the maxilla in an anterior direction involves what is called a reverse headgear. There are different ways that this is accomplished. The simplest way is to use elastic force against the upper fixed appliance with cemented brackets on the maxillary dentition. Another alternative to reverse headgear appliances is to attach the elastic force from the same facial mask with hooks or screws surgically attached directly to the maxilla itself. This type of reverse headgear is difficult and uncomfortable to wear, and the bone-supported screws are invasive and involve a surgical procedure. This technique, however, is very efficient in moving the maxilla in a forward direction and opening the nasopharyngeal airway.

Other techniques for expanding the nasal cavity by increasing airflow, such as by using a rapid expansion appliance (RPE), involve expanding the posterior maxillary arch. While such devices may leave the patient feeling as if they can breathe better through their nose, the devices require an invasive procedure that opens the midpalatal suture, as well as the installation of a midline palatal screw that is cemented to the teeth in the upper arch. Despite its invasive nature, the technique is very efficient at expanding the pallet, yet is usually restricted to patients that involve considerable expansion, for instance, greater than 6 mm. Moreover, the technique is not easily used on younger patients (e.g., below about four years of age) or on individuals where the intermaxillary, mid-palatal suture has closed (e.g., at about 15 years of age in females and about 17 years in males), as there is a remote possibility of fracturing other sutures, particularly in the cribriform area of the brain.

To create the expansion with an RPE appliance, the palatal screw is activated by quarter turns twice in the morning, which is equal to about 0.5 mm. Within three days, it is possible to observe an opening in the midline between the two upper central incisors with a slight space that indicates that the mid-palatal suture is opening with the procedure. For this procedure to be most effective, the maxillary intermaxillary suture should be open and capable of widening with relative ease.

Myofunctional therapy is another approach for the correction of breathing difficulties, such as improper tongue position, abnormal swallowing, mouth breathing, snoring, lack of nasal breathing, thumb sucking, improper resting tongue posture, and bruxism. However, as myofunctional therapy requires motivation and practice, it is often difficult getting young patients (e.g., less than four years of age) to achieve successful results, particularly as such patients often lack the necessary levels of cooperation and practice. To obtain about 1 to 2 hours of practice per day can be difficult and there remains many hours during the day, and especially at night, when the patient is not practicing proper function to obtain meaningful improvement. As a result, myofunctional therapy has little effect on the advancement of the maxilla.

It would be helpful, considering the advantages and disadvantages of the several above techniques, to have an appliance that can advance the maxilla to open up the nasopharyngeal airway, as well as to widen the upper posterior arch, which has the possibility of increasing nasal breathing. The present invention is intended to improve upon and resolve some of these known deficiencies of the art.

SUMMARY OF THE INVENTION

The present invention relates to an oral appliance for advancing the maxilla, as well as opening the nasopharyngeal airway in an effort to increase oxygen intake, while decreasing carbon dioxide retention. According to certain aspects herein, the oral appliance is a maxillary advancement appliance that is configured to advance, in an anterior direction, the premaxilla, the maxilla, and the maxillary dentition. In some illustrative embodiments, the appliance comprises a buccal shield in the maxillary posterior area, yet is devoid of a shield labial to the incisor area, while in accordance with other illustrative embodiments, the appliance includes an upper anterior shield that is separated from the labial surfaces of the maxillary incisors by several millimeters. The appliance may also include a lower portion for engaging the lower dentition with both labial, buccal and lingual shields, as well as extended lower lingual posterior shields to prevent the mandible from being distalized during sleep.

According to a first embodiment herein, the present invention is directed to a maxillary advancement appliance comprising a generally U-shaped upper body having an anterior portion configured to be adjacent to upper incisors and a posterior portion located rearward to the anterior portion. The upper body has an upper base with a perimeter defining an outer boundary and walls extending along the perimeter of the posterior portion of the upper body. The appliance further comprises a generally U-shaped lower body having an anterior portion configured to be adjacent to lower incisors, wherein the lower body has a lower base with a perimeter defining an outer boundary. In accordance with this embodiment, the lower base has a width that is configured to be greater than a width of the teeth of the user, and the lower body has walls extending along the perimeter of the lower body to define a trough. The trough is configured to contact the lower incisors as the appliance is worn in the mouth of the user. Moreover, the appliance also includes lingual protrusions extending rearward from the anterior portion of the upper body, wherein the lingual protrusions are configured to contact a maxilla when the appliance is worn within the mouth of the user.

In accordance with other aspects herein, the illustrative maxillary advancement appliance further comprises a raised surface on the posterior portion of the upper base of the upper body.

In accordance with still other aspects herein, the illustrative maxillary advancement appliance further comprises a shelf that projects generally horizontally from the upper body, the shelf being adjacent to the upper anterior base and being configured to extend rearward in the mouth of the user to provide a surface that is configured to guide a tongue as the appliance is worn within the mouth of the user.

In accordance with yet other aspects herein, the upper base of the illustrative maxillary advancement appliance is configured to contact the furthest forward upper teeth within the mouth.

According to other aspects herein, the illustrative maxillary advancement appliance further comprises a raised protrusion on one of the lingual protrusions, the raised protrusion being configured to direct a tongue as the appliance is worn within the mouth of the user.

In accordance with still other aspects herein, the illustrative maxillary advancement appliance further comprises a reline material exhibiting an adherence property that is configured to prevent the appliance from falling out of the mouth.

In accordance with other aspects herein, the illustrative maxillary advancement appliance is constructed from a resilient material, while in accordance to still other embodiments, the trough has a roughened surface.

According to certain embodiments herein, the lingual protrusions of the illustrative maxillary advancement appliance include a center tab extending rearward from a center of the anterior portion of the upper body and a side tab adjacent to each side of the center tab and extending rearward from the anterior portion of the upper body, wherein the center and side tabs are configured to move the maxilla and upper teeth forward with respect to the mouth in response to pressure from a tongue. In accordance with certain aspects herein, the side tabs are configured to encourage the tongue to exert pressure against the palatal tabs to encourage a widening of the palate.

According to other aspects herein, the illustrative maxillary advancement appliance further comprises palatal tabs on the posterior portion of the upper body, the palatal tabs being configured to receive pressure exerted by a tongue to encourage a widening of the palate.

In accordance with another embodiment herein, the present invention is directed to an orthodontic system worn adjacent to upper teeth and lower teeth in a mouth of a user, wherein the orthodontic system comprises an upper appliance having an anterior portion and a posterior portion located rearward of the anterior portion. The posterior portion is shaped to contact upper molars, and the upper appliance has an inner perimeter and an outer perimeter, wherein the outer perimeter is located exterior to the inner perimeter. The orthodontic system further comprises a lower appliance having an outer shield, wherein the outer shield extends vertically downward from the lower appliance to define a trough in the lower appliance, and further wherein the lower appliance is shaped to contact lower incisors and lower molars. The orthodontic system also includes a lining formed on at least a portion of the appliance, wherein the lining is configured to prevent the appliance from falling out of the mouth, as well as a ramp configured to extend around the inner perimeter and to contact upper incisors to move the maxilla and upper anterior teeth in a forward direction. The ramp has a first anterior end and a first posterior end located rearward with respect to the first anterior end, wherein the ramp extends rearward and diagonally from the inner perimeter of the upper appliance such that the first posterior end is positioned higher than the first anterior end. The orthodontic system also includes a tab having a second anterior end and a second posterior end located rearward with respect to the second anterior end, wherein the tab extends rearward and diagonally from the first posterior end of, and to a position higher than, the ramp such that the second posterior end is positioned higher than the second anterior end, and wherein the tab is configured to contact the upper jaw of the user and apply a force to move the upper jaw forward relative to the lower jaw as the appliance is worn within the mouth of the user. The system also includes a hinge that connects the upper appliance to the lower appliance.

In accordance with certain aspects herein, the illustrative orthodontic system further comprises a shelf in the upper appliance, wherein the shelf forms a cavity with the tab behind the anterior portion of the upper appliance.

According to still another embodiment herein, an illustrative appliance for correcting a malocclusion in the mouth of a user is provided, wherein, the appliance comprises a generally U-shaped upper body having an anterior portion configured to be adjacent to upper incisors and a posterior portion located rearward to the anterior portion, wherein the upper body has an outer perimeter and an inner perimeter that is located interior to the outer perimeter. The appliance further comprises a generally U-shaped lower body having an outer perimeter, wherein the outer perimeter of the lower body has an anterior portion adjacent to lower incisors and a posterior portion located rearward to the anterior portion of the lower body, the lower body having a lower labial shield extending along the outer perimeter of the lower body. The appliance also includes lingual protrusions that extend generally upward from the posterior portion of the inner perimeter of the upper body, wherein the lingual protrusions are configured to contact a palate of the user as the appliance is worn within the mouth of the user.

In accordance with another aspect of the present invention, an illustrative maxillary advancement appliance comprises an upper labial shield that is separated by several millimeters from the labial surface of the upper anterior teeth to aid in the elimination of mouth breathing, as well as to allow the anterior teeth and the maxilla to be advanced in a forward direction. In accordance with this specific embodiment, the shield is positioned in the labial direction from the upper incisors by several millimeters, such that the separation would allow the upper arch to be advanced without being restricted by the upper shield since it does not contact the upper labial surface of the front teeth.

In accordance with yet another aspect of the present invention, an illustrative maxillary advancement appliance is provided without a front upper labial shield. In accordance with this specific embodiment, the lack of the shield permits the upper incisors to come forward as desired.

According to another aspect of the present invention, an illustrative maxillary advancement appliance comprises at least one or more lingual tabs behind the upper front area of the dentition to move the maxilla and upper dentition in a forward direction when the patient's tongue applies force in a frontal direction. In accordance with certain aspects herein, the at least one or more lingual tabs are configured to receive force from the tongue to push the maxilla, premaxilla, and anterior dentition in a forward direction by as much as several millimeters.

According to still another aspect of the present invention, the illustrative maxillary advancement appliance comprises labial or anterior tabs configured to advance the maxilla, posterior palatal tabs configured to widen the maxilla, and lower lingual tabs configured to advance the mandible. In accordance with certain aspects herein, the upper posterior palatal tabs are configured to provide for expansion of the upper arch when the patient exerts pressure with the tongue laterally against the tabs. Moreover, in accordance with still further aspects herein, the lower lingual tabs are positioned lingual to the lower anterior dentition or lingual to the extension of the posterior lingual shields.

In accordance with other aspects herein, the illustrative maxillary advancement appliance comprises lower lingual tabs that are positioned towards the midline of the lower lingual front area of the appliance in order to prevent the lower jaw from slipping posteriorly while the user is sleeping. According to this specific aspect, the appliance is also configured to keep the mandible in an anterior position to thereby correct excessive overjet from occurring within the mouth.

According to certain embodiments herein, the upper and lower halves of the illustrative maxillary advancement appliance are lined with an acrylic, or other such plastic material, to increase the adherence of the appliance to the dentition, as well as to prevent the appliance from being dislodged during use. In accordance with this embodiment, in order for the liner material to adhere the appliance to the dentition, the interior trough of the appliance can be further textured or roughened as desired. Moreover, in accordance with certain embodiments, the liner can be individually placed in either the upper or lower posterior segments, the upper or lower anterior segments, or within only one-half of the appliance.

In accordance with certain aspects herein, the present invention provides an appliance, system and method for advancing a maxillary complex in such a manner that the nasopharyngeal airway is opened as a result. According to certain specific illustrative embodiments herein, the appliance can be configured to advance the maxillary complex on only one side as desired.

In accordance with yet another aspect of the present invention, the illustrative maxillary advancement appliance is configured to widen the posterior upper arch or lower arch.

In accordance with still another aspect of the present invention, the illustrative maxillary advancement appliance is configured to retain the upper or lower arches by lining the trough or troughs in order to be well retained to the specific arch.

In accordance with another aspect of the present invention, the illustrative maxillary advancement appliance is configured to encourage the tongue to rest in its proper position within the palatal area.

In accordance with still another aspect of the present invention, the illustrative maxillary advancement appliance is configured to encourage the mandible to be held in a forward, normal anteroposterior position (relative to the age of the patient) to prevent the lower jaw from slipping posteriorly during sleep, thereby closing or partially closing the oral pharyngeal airway.

In accordance with another aspect of the present invention, the illustrative maxillary advancement appliance is configured to fit various age groups depending on the presence of the posterior molars.

In accordance with yet another aspect of the present invention, the illustrative maxillary advancement appliance is configured to guide the pre-maxilla and anterior dentition to proceed in a downward and forward direction.

In accordance with still another aspect of the present invention, the illustrative maxillary advancement appliance is configured to eliminate mouth breathing and encourage nasal breathing.

According to certain other aspects herein, the illustrative maxillary advancement appliance is configured to be worn interchangeably and alternately with other oral appliances without interfering with the tooth movement capabilities of the other oral appliances.

Additional features and advantages of the present invention are described in, and will be apparent from, the detailed description of the presently preferred embodiments and from the drawings.

DETAILED DESCRIPTION

Figure 1:
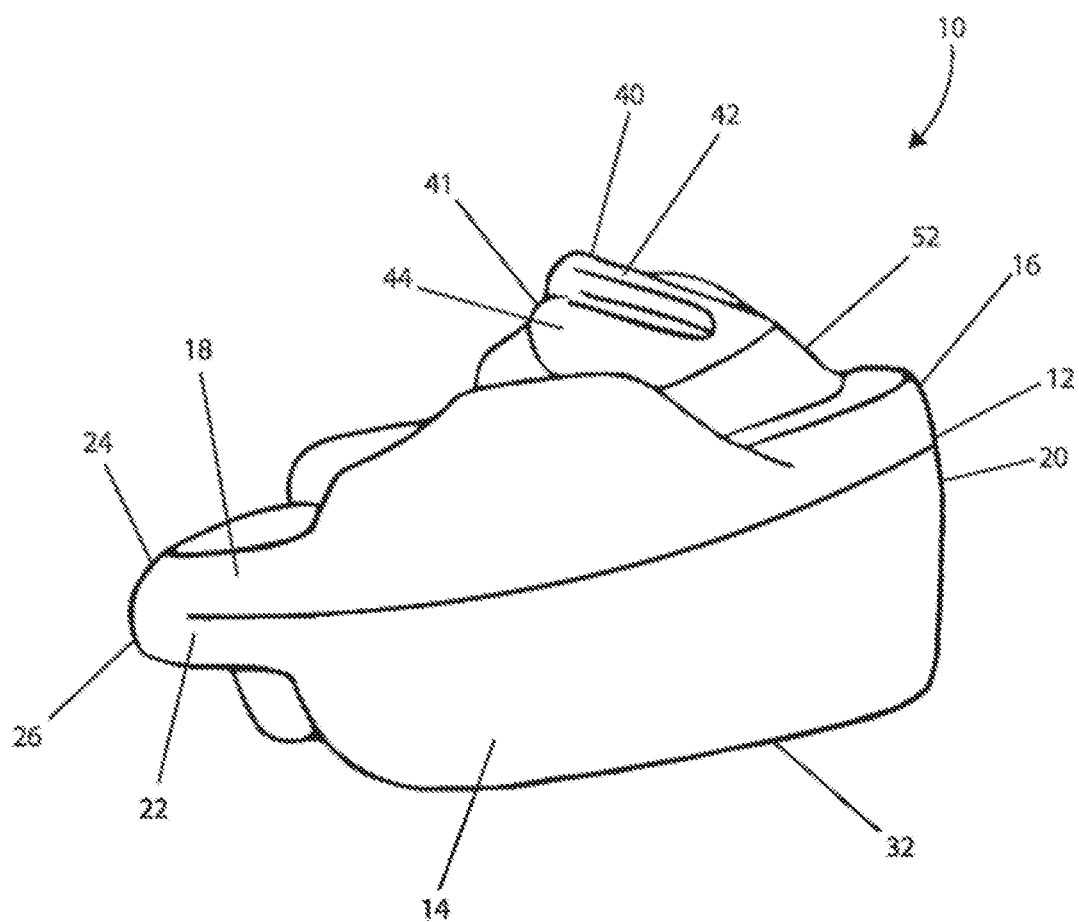
FIG. 1 illustrates a side view of an oral appliance in an embodiment of the present invention.
Figure 2:
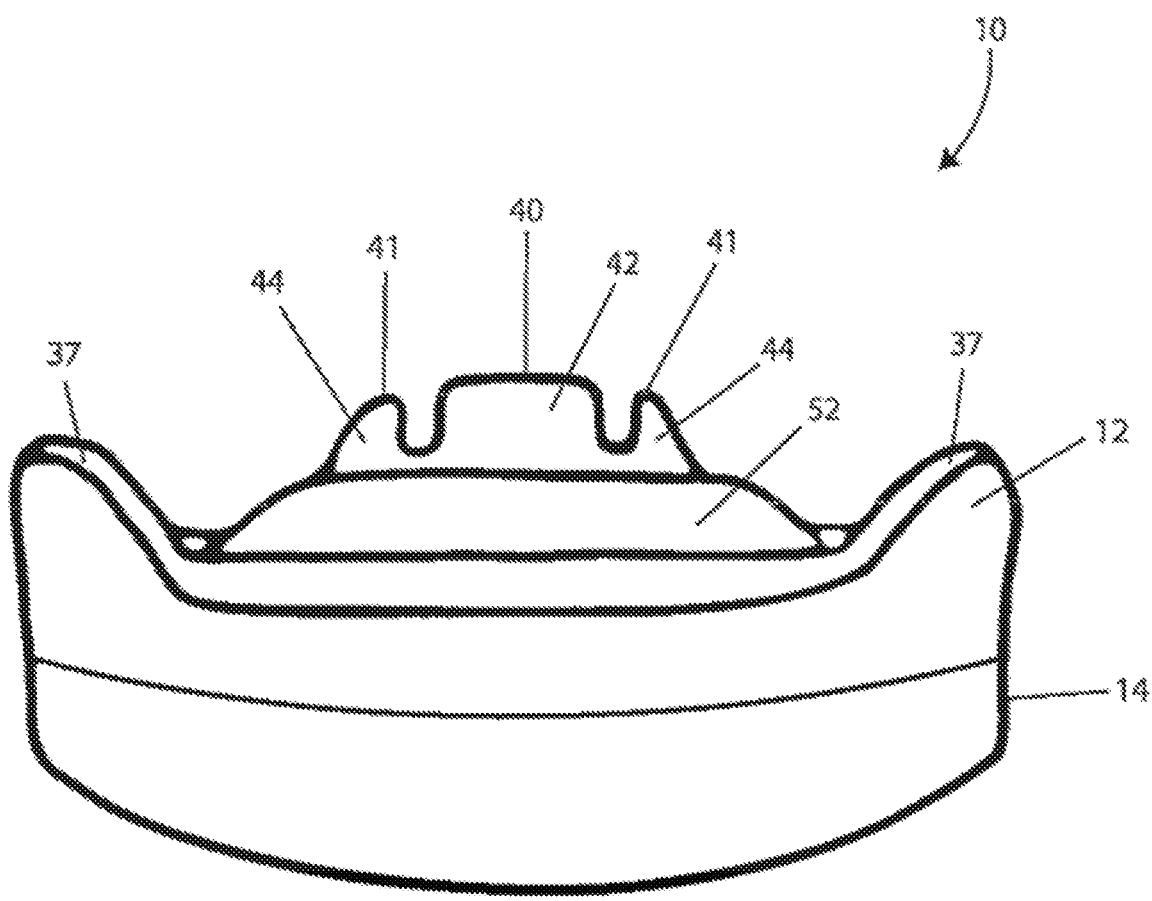
FIG. 2 illustrates a front view of an oral appliance in an embodiment of the present invention.
Figure 3:
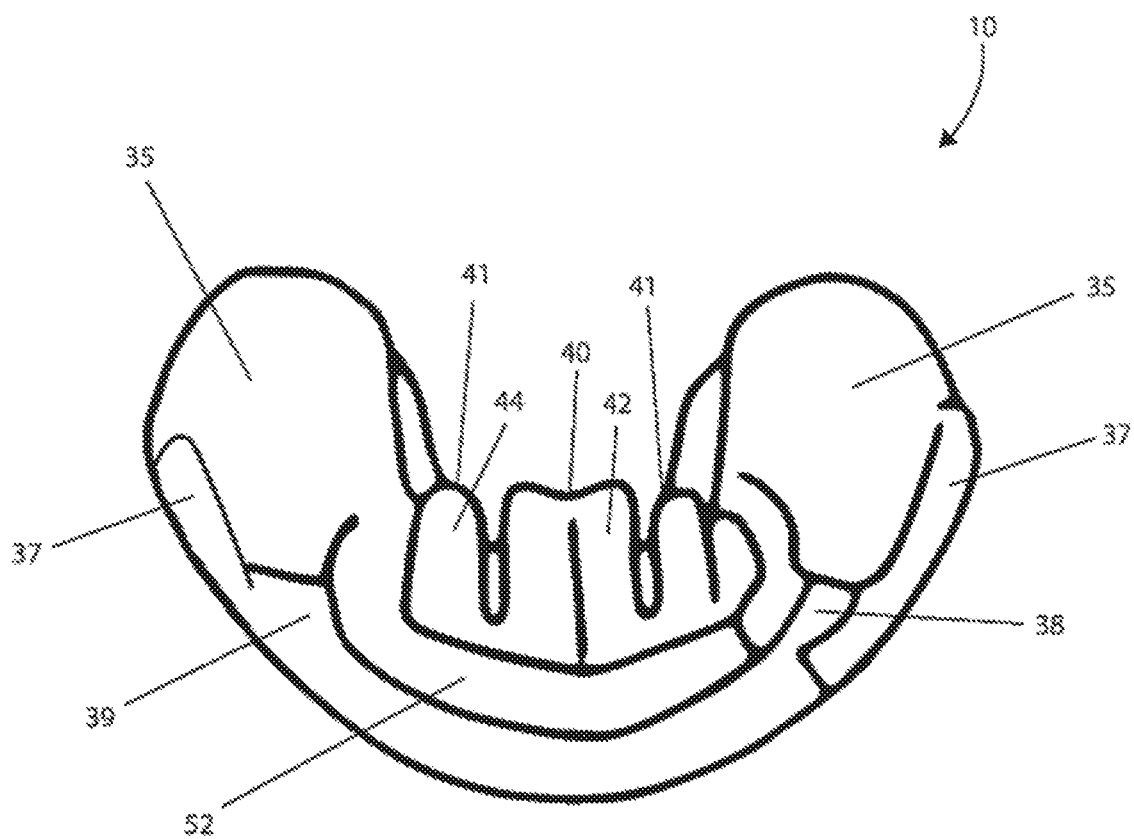
FIG. 3 illustrates a top view of an oral appliance in an embodiment of the present invention.

The present invention relates to a dental appliance, system and method for advancing the maxilla and the maxillary dentition in order to increase the nasopharyngeal airway. This appliance design can increase the air exchange, specifically the oxygen intake, which increases the oxygen to the brain the immune system and the endocrine systems as well as reducing carbon dioxide retention.

In accordance with certain aspects herein, the appliance may be preformed or customized to the patient's dentition, as well as may be designed to fit patients of various ages. In accordance with specific embodiments, the size of the appliance can be dependent upon and customized to accommodate the teeth present in the patient's mouth at the time of treatment. For instance, for an appliance designed for a two-year-old, the device can be customized based upon whether or not the deciduous second molars are present. If these deciduous second molars are present, the length of appliance could be customized, for instance, to accommodate patients up to about six years of age or until the first permanent molars have erupted. Once the first permanent molars have erected, another sized appliance could then be implemented for use up to about 12 years of age. Finally, once the second permanent molars have erected, another sized appliance could be implemented to accommodate most individuals over 12 years of age.

Referring now to the drawings, wherein like numerals refer to like parts, FIGS. 1-6 illustrate various views of an embodiment of an appliance 10 for dental and/or orthodontic use in a mouth of a patient. The appliance 10 may be worn by a patient of approximately three years to eight years of age. However, patients of other ages may also use the appliance 10. The appliance 10 may be constructed from rubber, plastic, silicone and/or like material. The appliance 10 may be constructed from a resilient material. The resiliency of the appliance 10 may improve the comfort and/or performance of the device for the patient when worn in the mouth.

In an embodiment, the appliance 10 may have an upper body 12 and a lower body 14. The upper body 12 and/or the lower body 14 may be generally U-shaped to correspond to the oral anatomy of the patient and/or fit within the mouth of the patient. Of course, the shape of the upper body 12 and/or the lower body 14 may be configured in a variety of shapes to fit variations in oral anatomy of patients. The variations in oral anatomy of patients may be due to mouth size, mouth shape, arch of the dentition of the patient, age of the patient, ethnicity of the patient and the like. Thus, the general U-shape of the upper body 12 and/or the lower body 14 may be narrowed, broadened, lengthened and/or shortened depending on the patient. The shape of the upper body 12 and/or the lower body 14 may be designed for the anatomy of any patient.

The upper body 12 may have an anterior portion 16 and a posterior portion 18 located opposite the anterior portion 16. The anterior portion 16 may be positioned near and/or at a front of the oral cavity of the patient when the appliance 10 is worn by the patient. The posterior portion 18 may be positioned furthest within the oral cavity of the patient when the appliance 10 is worn by the patient. Thus, the anterior portion 16 of the upper body 12 may be located adjacent to the labial area behind the lips in the front of the mouth of the patient. The upper body 12 may be located adjacent to the upper teeth in the upper jaw, maxilla and palate of the patient when the appliance 10 may be worn in the mouth of the patient.

The lower body 14 may also have an anterior portion 20 and a posterior portion 22 located opposite the anterior portion 20. The anterior portion 20 may be positioned near and/or at a front of the oral cavity of the patient when the appliance 10 may be worn by the patient. The posterior portion 22 may be positioned furthest within the oral cavity of the patient when the appliance 10 is worn by the patient. Thus, the anterior portion 20 of the lower body 14 may be located adjacent to the labial area behind the lips in the front of the mouth of the patient. The lower body 14 may be located adjacent to the lower teeth in the lower jaw and/or mandible of the patient when the appliance is worn in the mouth of the patient.

The posterior portion 18 of the upper body 12 may have posterior ends 24. The posterior ends 24 of the posterior portion 18 of the upper body 12 may be positioned furthest with the oral cavity and/or near a rear of the oral cavity of the patient when the appliance 10 is worn by the patient. Thus, the posterior ends 24 of the upper body 12 may be located near the back of the mouth near the upper molars of the patient.

The posterior portion 22 of the lower body 14 may also have posterior ends 26. The posterior ends 26 of the posterior portion 22 of the lower body 14 may be positioned furthest with the oral cavity and/or near a rear of the oral cavity of the patient when the appliance 10 is worn by the patient. Thus, the posterior ends 26 of the lower body 14 may be located near the back of the mouth near the lower molars of the patient.

In an embodiment of the invention, the appliance 10 may be designed to advance the maxilla by the patient pressing the tongue against the anterior portion of the maxilla, which may advance the upper jaw forward. In an embodiment, the upper body 12 of the appliance 10 may have an upper base 30, and the lower body 14 may have a lower base 31. The upper base 30 may receive the upper teeth of the patient and the lower base 31 may receive the lower teeth of the patient. The lower base 31 may also have a lower labial shield 32. However, no labial shield may be provided on the upper base 30.

Depending on the shape and/or size of the appliance 10 with respect to the oral cavity and the upper dentition of the patient, some of the upper teeth may not contact and/or fit within and/or on the upper base 30. In addition, the upper base 30 may have an elevated portion 35. The elevated portion 35 may be located near the posterior portion 18 of the upper body 12 of the appliance 10. The elevated portion 35 may extend from the posterior ends 24 in an anterior direction toward the anterior portion 16 of the upper body 12. The upper body 12 may also have upper walls 37 attached to the upper body 12. The upper walls 37 may extend vertically upward from an outer periphery of the posterior portion 18 of each of an upper left side surface 38 and an upper right side surface 39 on the upper base 30 of the upper body 12. The upper base 30 may receive some and/or all of the upper dentition. The upper posterior teeth, for example, molars, may fit on the upper base 30 within the upper walls 37. When the patient may wear the appliance 10, the elevated portion 35 may depress the upper posterior teeth. The depression of the upper posterior dentition may deepen the bite of the patient by also encouraging the upper front teeth to erupt.

In addition, the upper walls 37 may also provide an increased level of safety for the patient. For example, the upper walls 37 may increase the physical size of the appliance 10 so that the upper walls 37 may inhibit excessive and/or unwanted movement of the appliance 10 within the mouth of the patient. In addition, the upper walls 37 may inhibit the appliance 10 from being swallowed.

To augment the advancement of the maxilla, an embodiment of the appliance 10 may also have protrusions and/or tabs extending in an upward and/or rearward orientation in three areas, for example. Moreover, in accordance with certain aspects herein, one or more tabs can be positioned lingual to the upper anterior dentition and extending up into the palate to cause the tongue to advance the anterior arch. In accordance with this embodiment, the appliance 10 can include a central tab 40, and two lateral tabs 41 that allow the tongue to exert force in different directions to the maxillary area. According to certain aspects herein, posterior palatal tabs 72 can also be included to allow the posterior dental arch and maxillary area to widen with lateral tongue pressure, thereby increasing nasal air intake. In accordance with certain aspects herein, the appliance 10 can be configured such that the tongue can place pressure only on one of the tabs to increase a cross by area on one side when one does not exist on the opposite side. Moreover, in accordance with other alternative embodiments, the appliance 10 can be configured such that the patient is capable of expanding their tongue in a forward direction, as well as in a lateral direction to one side or the other, to increase the entire maxillary alveolar area and to advance the maxilla at the same time. It should be understood and appreciated herein that if the entire maxillary area requires advancement, it is advisable to have the tongue pressure as high as possible against the pre-maxillary area. If the advancement is required only on one side, however, the tongue pressure is exerted only on that side. It should also be understood and appreciated herein that a similar situation exists in the posterior area in the upper arch where bilateral expansion is needed. The tongue pressure is therefore made equally on both sides of the upper arch against both palatal posterior maxillary tabs. If there is narrowing or a cross bite only on one side, the tongue pressure is concentrated only on the one side requiring the correction.

It should be understood herein that those of skill in the art would appreciate that any number of tabs can be placed in the upper anterior segment. Moreover, as will be explained in detail below, it should also be understood and appreciated herein that bumps or protrusions (such as reminder bumps 47) can also be fabricated onto the tabs to indicate to the patient where their tongue should be placed for purposes of exerting pressure. It should also be understood herein that the tabs 40, 41 and 72, whether positioned posteriorly or anteriorly, can be of various shapes and sizes in order to more efficiently provide widening of the posterior palatal area or to advance the maxilla in the anterior area. Moreover, in accordance with certain aspects herein, the tabs can be removed or cut away from the appliance 10 once the patient knows where to place their tongue during use of the appliance.

In accordance with certain embodiments in which expansion is only necessary on one side of the anterior arch, the patient can be instructed to place tongue pressure on that side in order to equalize the anterior arch. According to this aspect of the present invention, if the patient has a recessed midface, the same anterior tabs may be used by instructing the patient to position the tongue rather high in the palate and exert force in this area to advance the midface.

In accordance with certain aspects herein, tabs, similar to tabs 40, 41, can serve as lower lingual tabs that are configured to keep the mandible in an anterior position while sleeping, thereby preventing the mandible from being distalized when the muscles relax, as well as keeping the tongue in an anterior position to thereby prevent closure of the oropharyngeal airway. As those of skill in the art will understand herein, since the genioglossus muscle of the tongue is connected to the mandible via the genial tubercles of the lower jaw, when the lower jaw is allowed to drift posteriorly during sleep, the tongue is also allowed to drift posteriorly at the same time. As a result, the tongue can impinge on the oral pharyngeal airway, thereby causing its partial or complete closure. If the mandible can be prevented from drifting distally while sleeping (particularly during open mouth breathing), the tongue is also prevented from drifting distally. Accordingly, if the oral appliance 10 can prevent the lower jaw from drifting posteriorly, it will also prevent the tongue from drifting in the same way, and as a result, will permit the oropharyngeal airway to remain opened.

In accordance with certain aspects herein, the lower lingual tabs are configured to hold the mandible in an anterior position, thereby preventing it from posturing or drifting posteriorly while sleeping.

According to a certain embodiment herein, the anterior area of the oral appliance 10 is slanted downward and forward to encourage the incisors and the pre-maxillary area to proceed with a desired inclination rate that is typical of a maxillary area. In addition, in accordance with certain aspects, the appliance 10 may be preformed to fit several mouth sizes, as well as may be customized to fit a specific patient's mouth.

In another embodiment, the interior trough of the appliance 10 on the upper and/or lower arch may be a textured or roughened to receive a liner material, which makes the appliance more attentive to the dental arch, as well as prevents it from falling out of the mouth or from being unconsciously removed while sleeping.

In accordance with certain aspects herein, the appliance may have the upper 12 and lower 14 halves sealed together, which tends to force the patient to breathe through their nose, thereby eliminating mouth breathing.

In an embodiment, central tab 40 may be provided by and above the upper central incisors of the patient. In addition, side tabs 41 are provided on each side of the central tab 40. The side tabs 41 may be lingual to and/or above the upper laterals and/or canines on each side of the interior of the mouth of the patient. Thus, three tabs 40, 41 may be provided in an embodiment. However, the invention is not limited to a certain number of tabs and other numbers of tabs may be provided within the scope of this present invention.

The central tab 40 may have a front surface 42 and a rear surface 43. The front surface 42 of the central tab 40 may be generally planar. Similarly, the side tabs 41 may have a front surface 44 and/or a rear surface 45. The front surface 44 of the side tabs 41 may also be generally planar.

When the appliance 10 may be worn by the patient, the front surface 42 of the central tab 40 and/or the front surface 44 of one and/or both of the side tabs 41 may contact the maxilla. The combination of the front surface 42 of the central tab 40 and the front surface 44 of one and/or both of the side tabs 41 on the upper portion of the body 15 may push across the whole segment of the maxilla. Thus, the combination of the front surface 42 of the central tab 40 and/or the front surface 44 of one and/or both of the side tabs 41 may create pressure that is more complete across the whole area of the pre-maxillary region.

Figure 4:
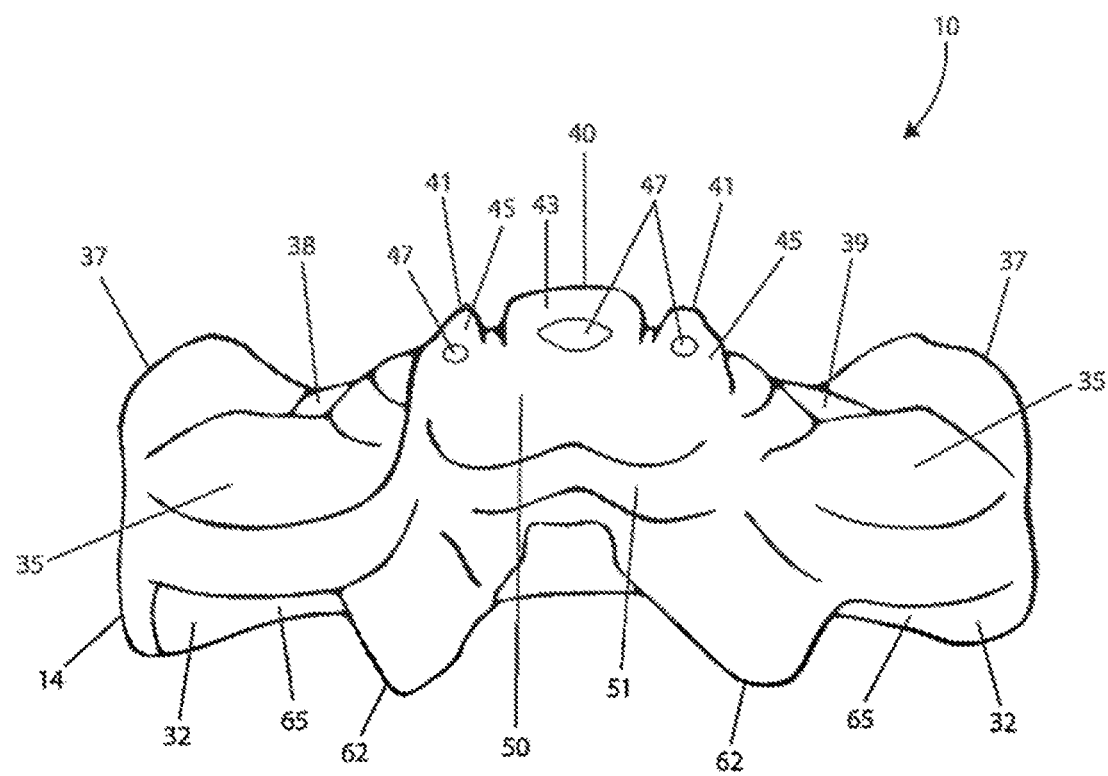
FIG. 4 illustrates a rear view of an oral appliance in an embodiment of the present invention.

In an embodiment shown in FIG. 4, reminder bumps 47 may be located at an upper margin on the rear surface 43 of the central tab 40 and/or at an upper margin on the rear surface 45 of one and/or both of the side tabs 41. The reminder bumps 47 may be integrally formed on the rear surface 43 of the central tab 40 and/or at an upper margin on the rear surface 45 of one and/or both of the side tabs 41. The reminder bumps 47 may be a raised protrusion detectable by the tongue of the patient. The reminder bumps 47 may have a generally round, oval, oblong and/or triangular shape. However, any shape may be used. Thus, the reminder bumps 47 may be used as a guide for the patient when the appliance 10 may be worn by the patient.

For example, the tongue of the patient may feel for the reminder bumps 47 on the rear surface 43 of the central tab 40 and/or one and/or both of the reminder bumps 47 on one and/or both of the rear surface 45 of the side tabs 41. The reminder bumps 47 may provide a convenient indication for the patient of a proper region of the appliance 10 on which to exert pressure.

Further, the appliance 10 may have an upper anterior lingual section 50 located near the central tab 40 and/or the side tabs 41. The tongue of the patient may push against the reminder bumps 47 on the rear surface 43 of the central tab 40 and/or the rear surface 45 of one and/or both of the side tabs 41. The pressure that may be generated by the tongue of the patient against the rear surface 43 of the central tab 40 and/or the rear surface 45 of one and/or both of the side tabs 41 may cause the front surface 42 of the central tab 40 and/or the front surface 44 of one and/or both of the side tabs 41 to contact the anterior portion of the palate of the patient. Thus, the pressure exerted by the tongue of the patient may translate forward against the anterior portion of the palate to push the palate forward. The pressure generated from this activity may advance the entire maxilla in the proper area. Further, the tongue pushing against the maxilla may open the transverse palatal suture to allow the whole maxilla to be pushed in an anterior and/or forward position. The pushing of the tongue in this manner may assist with correcting the Class III mandibular overgrowth in patients of a young age, in particular.

In an embodiment, the upper anterior lingual section 50 of the appliance 10 may have a shelf 51. The shelf 51 may be located below the rear surface 43 of the central tab 40 and/or the rear surface 45 of one and/or both of the side tabs 41. The shelf 51 may slant forward and upward to guide the tongue upward to the highest position for accurate positioning of the appliance 10 against the anterior palate and the maxilla of the patient. Thus, in addition to the reminder bumps 47 on the rear surface 43 of the central tab 40 and/or one and/or both of the reminder bumps 47 on one and/or both of the rear surface 45 of the side tabs 41, the gradual incline on the shelf 51 of the upper lingual section 50 may also be used to guide the tongue to advance the entire maxilla in the proper direction.

In accordance with certain aspects herein, the shelf 51 may be slanted slightly downward to encourage the tongue to assume a more elevated normal position within the palate of the upper arch, as well as to forwardly guide the incisors and maxilla to mimic the natural direction of growth in the midface. According this illustrative embodiment, it should be understood and appreciated herein that the area for the tongue within the palate can be configured smaller and narrower in the lower arch to make the appliance uncomfortable for a user to abnormally retain their tongue within the body of the mandible.

Further, a ramp 52 may extend at an angle relative to the upper base 30 on the anterior portion 20 of the upper body 12. The ramp 52 may exert a force on the upper incisors and may guide the upper incisors forward and downward when the appliance 10 is worn within the mouth of the patient. The angle of the ramp 52 may guide the upper incisors forward and/or downward to increase overjet and/or overbite of the patient. Doing so may also assist with correcting the Class III mandibular overgrowth in patients of a young age.

Figure 5:
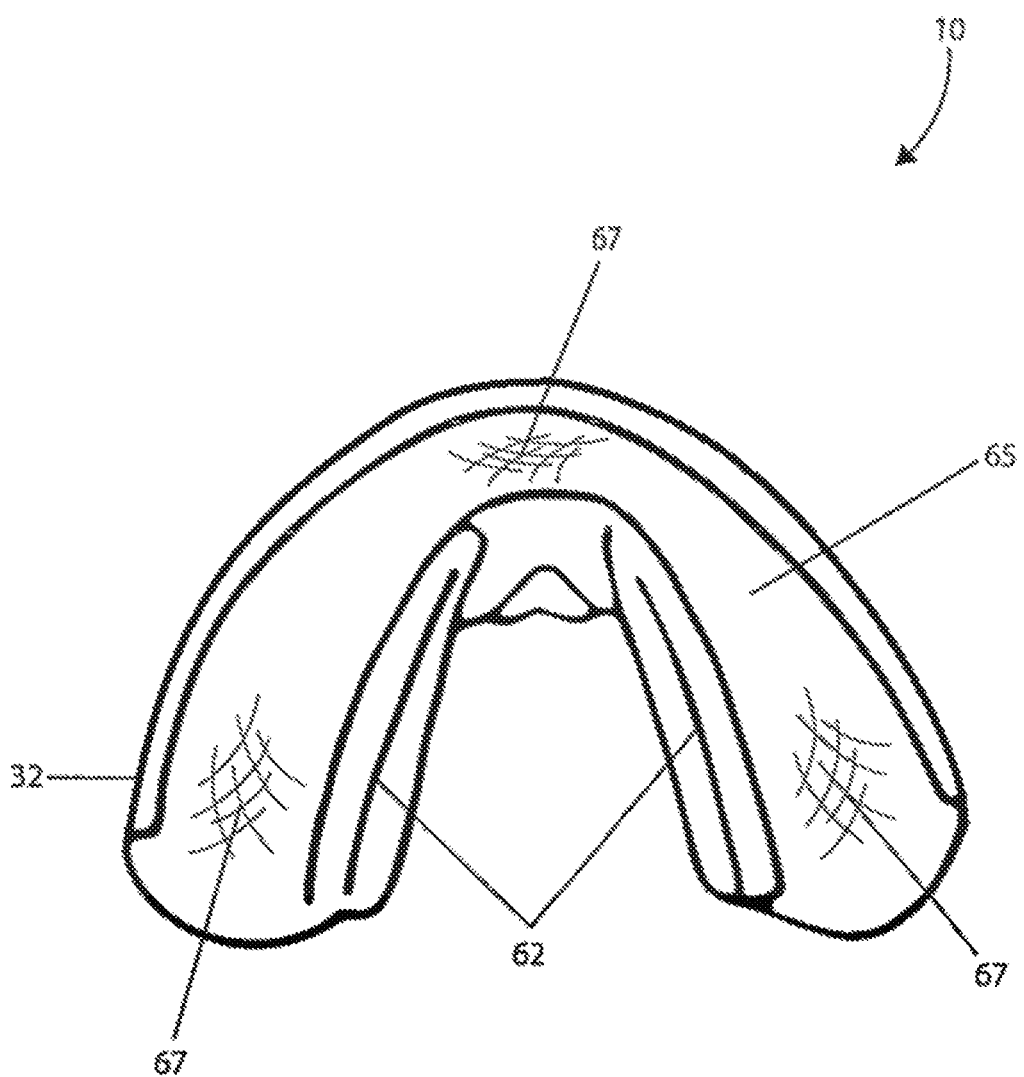
FIG. 5 illustrates a bottom view of an oral appliance in an embodiment of the present invention.

Referring now to FIGS. 4 and 5, in an embodiment, the lower body 14 of the appliance 10 may have the lower labial shield 32 arranged at an outer periphery of the lower body 14. The lower body 14 may also have inner ridges 62. The lower labial shield 32 and the inner ridges 62 may define a lower trough 65. The lower trough 65 may receive some and/or all of the lower dentition of the patient when the appliance 10 may be worn in the mouth of the patient. Depending on the shape and/or size of the appliance 10 with respect to the oral cavity and the lower dentition of the patient, some of the lower teeth may not fit within the lower trough 65.

As shown in the figures, the lower body 14 may be combined with the upper body 12 to form the appliance 10. The lower trough 65 formed in the lower base 31 of the appliance 10 may be defined by the lower labial shield 32 on the outer periphery of the lower body 14 and by the inner ridges 62 at the inner periphery of the lower body 14.

Figure 6:
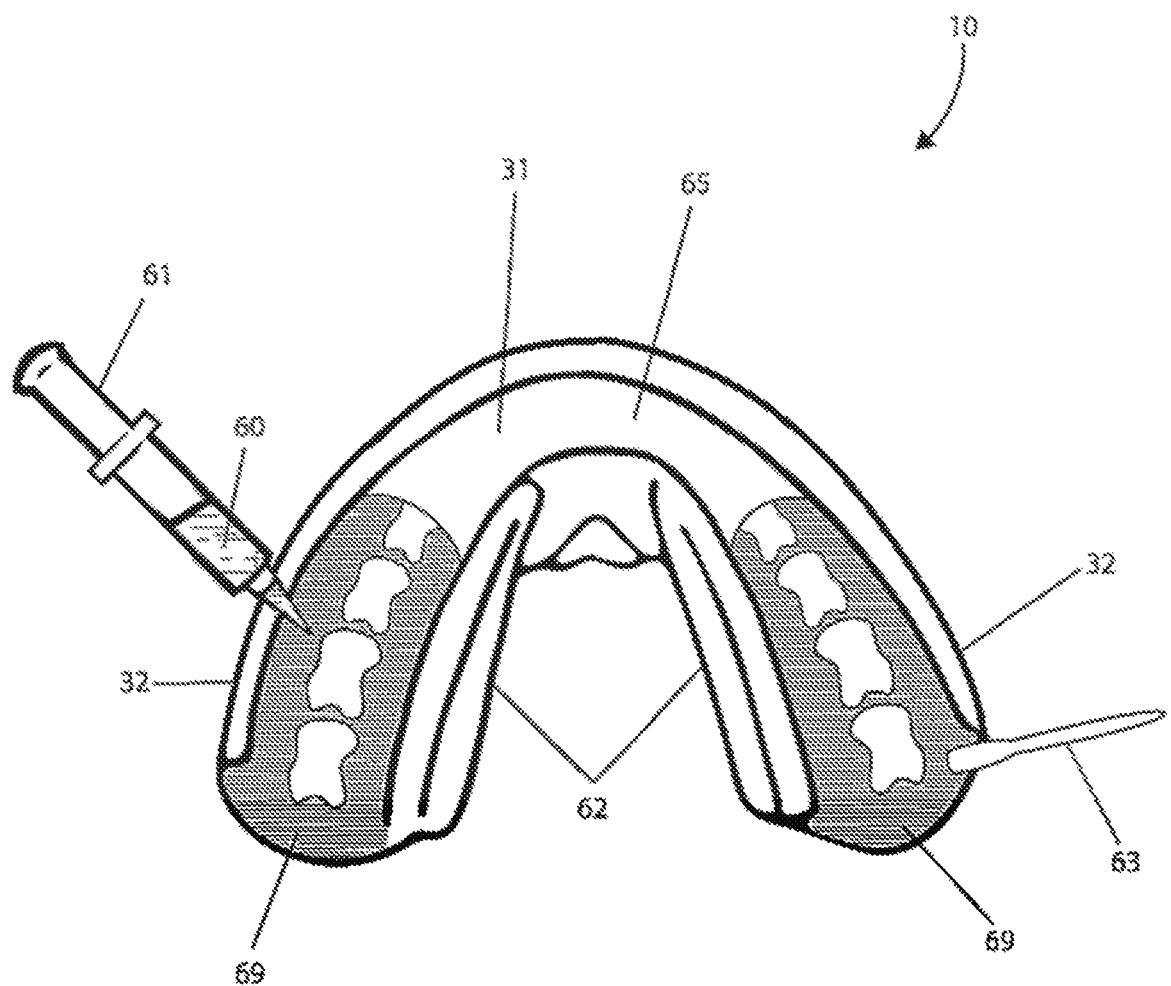
FIG. 6 illustrates a bottom view of an oral appliance in an embodiment of the present invention.

In an embodiment, a method may be provided which may increase retention of the appliance 10 in the mouth of the patient and/or the effectiveness of the correction of the malocclusion using the appliance 10. For example, the lower trough 65 on the lower base 31 of the lower body 14 may receive a reline material 60, as illustrated in FIG. 6. The reline material 60 may be a self-cure acrylic, for example. In an embodiment, the reline material 60 may be injected from, for example, a syringe 61. The reline material 60 may also be applied, for example, using a spatula 63 to spread the reline material 60 on the lower trough 65, as desired.

In an embodiment, the lower base 31 of the lower body 14 of the appliance 10 may have textured, coarse and/or roughened surfaces 67, hereinafter, surfaces 67. The surfaces 67 may be located on the lower trough 65 within and/or along the lower labial shield 32 and/or the inner ridges 62. The surfaces 67 may secure the reline material 60. The surfaces 67 may prevent the reline material 60 from becoming disengaged from the lower base 31. The surfaces 67 may provide for better adherence of the reline material 60 to the lower trough 65 of the appliance 10. After inserting the reline material 60 onto the surfaces 67 of the lower trough 65, the appliance 10 may be placed in the mouth of the patient. The appliance 10 may be pressed forcibly against the lower teeth of the patient. In particular, the lower base 31 may be forcibly pushed down on the lower teeth. The patient may also then bite down to maintain the appliance 10 under pressure until the reline material 60 has set. When the reline material 60 may be set, the appliance 10 may be removed from the mouth of the patient.

In an embodiment, the reline material 60 may be allowed to harden in the mouth of the patient for 2½ minutes, for example. The reline material 60 may flow around and at least partially surround and/or encapsulate the lower dentition to form a lining 69 of hardened reline material 60. The lining 69 of hardened reline material 60 may be form-fitting lining on at least some of the posterior lower teeth as shown in FIG.

6. The lining 69 may provide a more secure and/or snug fit between the appliance 10 and the lower dentition of the patient. Thus, the reline material 60 may secure the appliance 10 to the teeth of the patient when hardened into the lining 69. A purpose of the lining 69 may be to allow the whole lower dentition of the patient to be moved in a distal and/or rearward direction when the appliance 10 may be worn in the mouth of the patient.

The reline material 60 may be placed on the appliance 10 in any areas in which teeth may be contacted. For example, in certain cases where indicated, the lower front teeth, for example, incisors, in the front of the lower trough 65 may also be lined with the reline material 60. Thus, the lower front teeth may be permitted to be moved without being tipped when being moved in a rearward direction. In other cases, however, the lower front teeth in the front of the lower trough 65 may not be lined with the reline material 60. For example, in cases of crowding of the lower front teeth, it may be preferred to not line the lower front teeth in the front of the lower trough 65 with the reline material 60. Thus, the posterior lower teeth may be distalized and/or moved in a rearward direction which may provide more room for the front lower teeth to move which may alleviate the crowding of the lower front teeth.

In an embodiment, the appliance 10 may be hinged as shown in FIG. 1. The lower body 14 may be joined with the upper body 12 near the posterior ends 26 to allow the opening of the upper jaw and/or the lower jaw of the patient. The hinged appliance 10 may provide an increased level of comfort to the patient. In particular, when a young child may wear the appliance 10 in the mouth, the appliance 10 may be stabilized in the mouth of the patient. The hinged construction of the appliance 10 may also provide an increased level of safety to the patient. For example, the hinged construction of the appliance 10 may inhibit excessive and/or unwanted movement of the appliance 10 within the mouth of the patient and/or may inhibit aspiration of the appliance 10.

Accordingly, the appliance 10 may be worn by the patient at night while the patient is lounging, resting and/or sleeping, for example. However, use of the appliance 10 during waking hours may enhance the correction and/or shorten the time required for correction of the malocclusion. Preferably, the patient may wear the appliance 10 while sleeping and two hours during the day when pushing the tongue against the upper anterior portion of the palate.

The patient may perform exercises which may correct malocclusions while requiring a lesser amount of cooperation than required with known appliances. To this end, the patient may press the tongue forward against the reminder bumps 47 on the rear surface 43 of the central tab 40 and/or one and/or both of the reminder bumps 47 on one and/or both of the rear surface 45 of the side tabs 41. Further, movement of the teeth may reduce an amount of exercise or other cooperation required for correction of the malocclusion. If space is required within the mouth of the patient due to crowding of teeth, one or more teeth may be stripped and/or removed prior to wearing of the appliance 10.

As a result, the patient may reduce a need for wearing the appliance during, for example, the daytime when the patient is awake or active. However, an overall time period during which a malocclusion is corrected may be extended. In an example, the overall time period for the patient to correct the malocclusion may be extended from a period of four months to ten months to a period of two years or more with reduced wearing of the appliance during the time the patient is awake or active.

Figure 7:
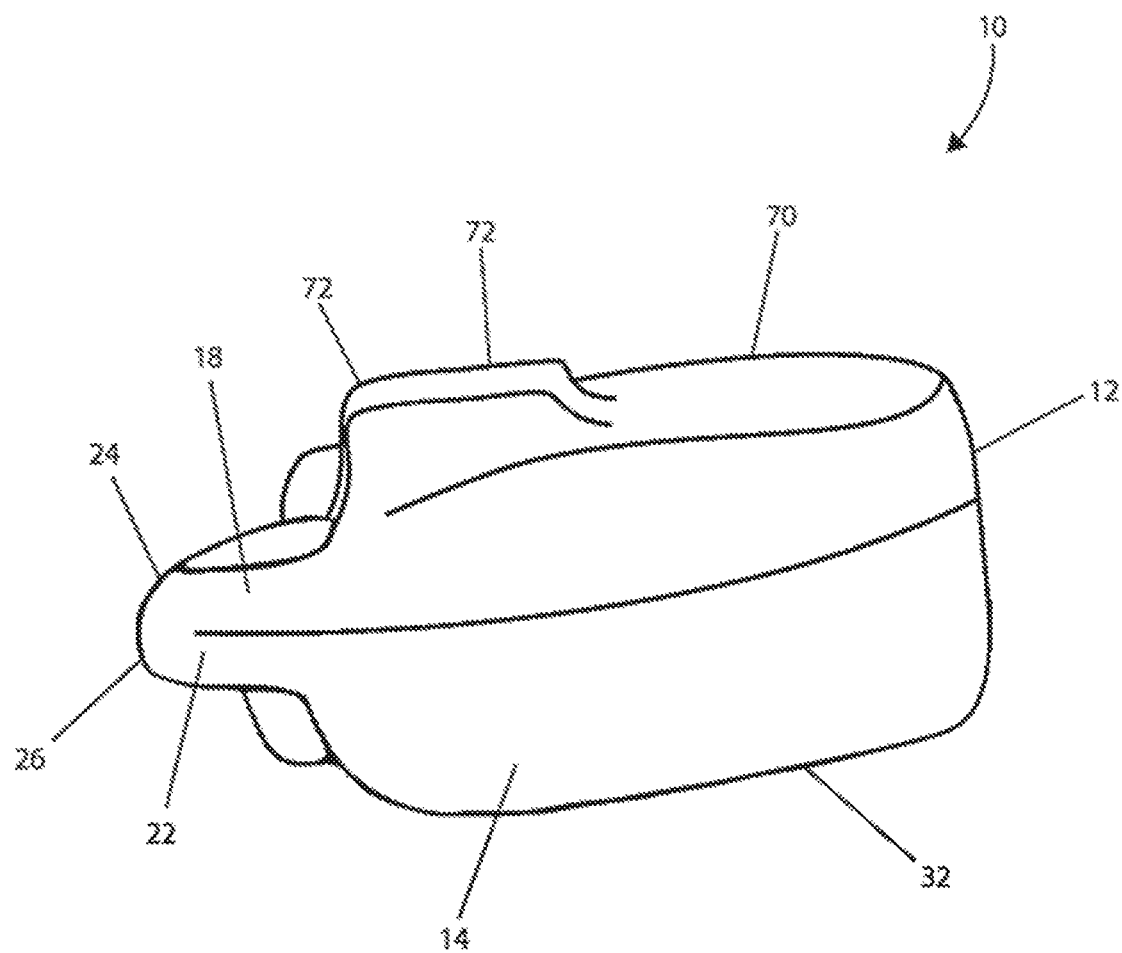
FIG. 7 illustrates a side view of an oral appliance in an embodiment of the present invention.
Figure 8:
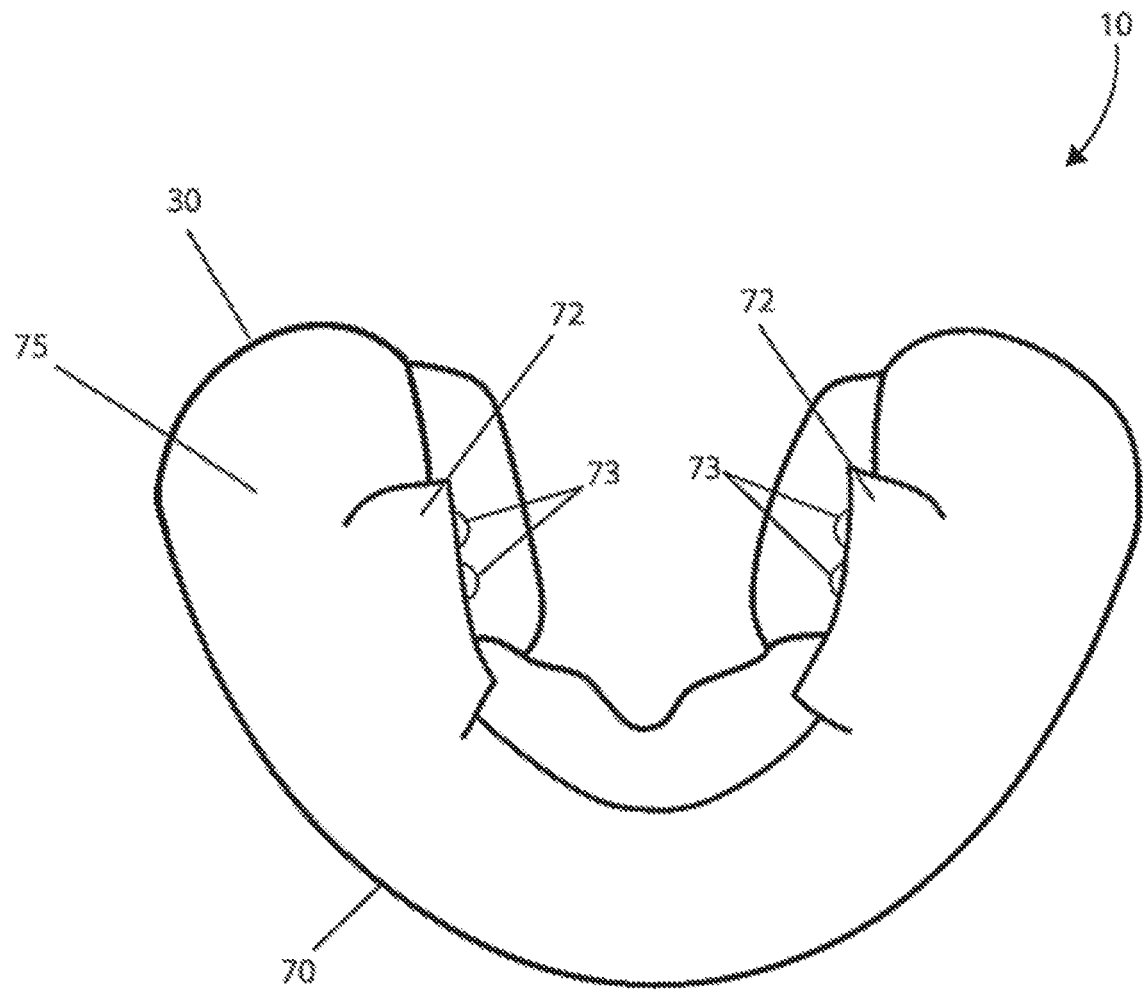
FIG. 8 illustrates a top view of an oral appliance in an embodiment of the present invention.
Figure 9:
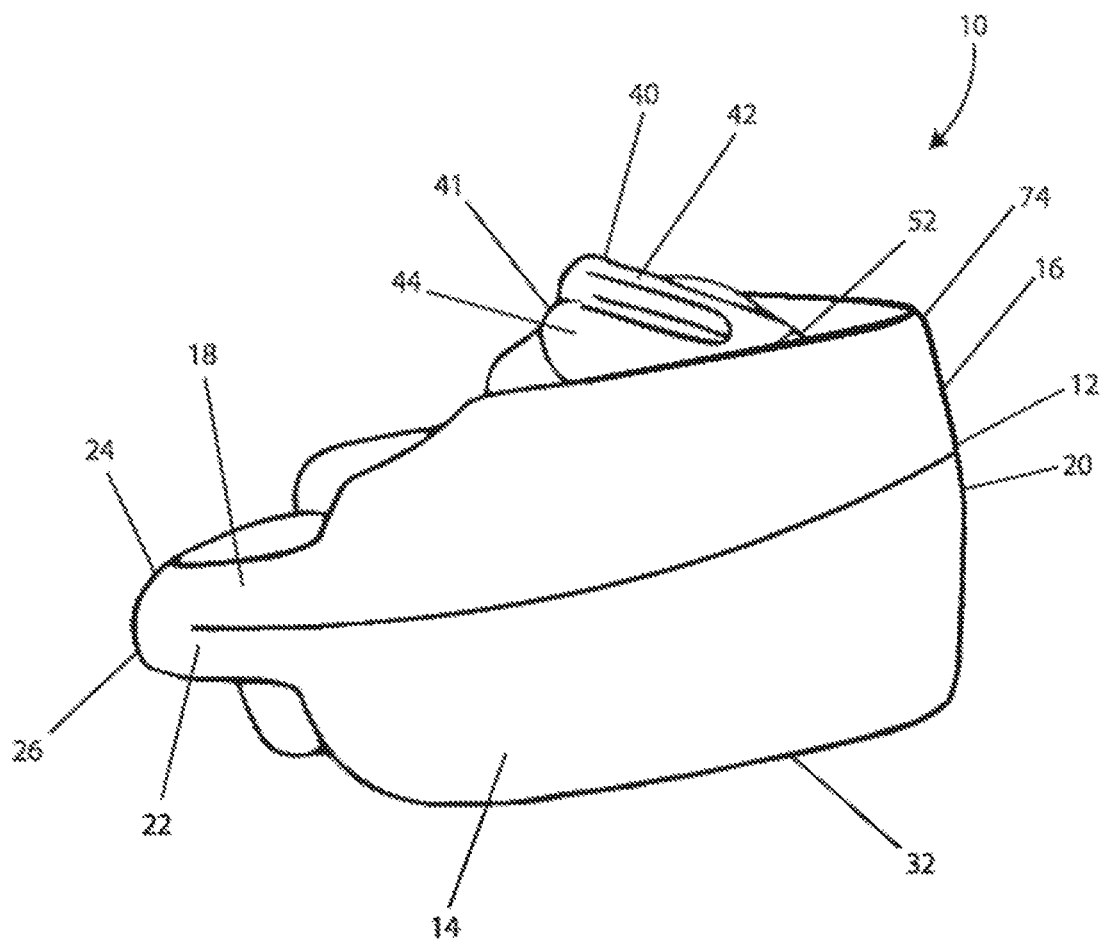
FIG. 9 illustrates a side view of an oral appliance in an embodiment of the present invention.
Figure 10:
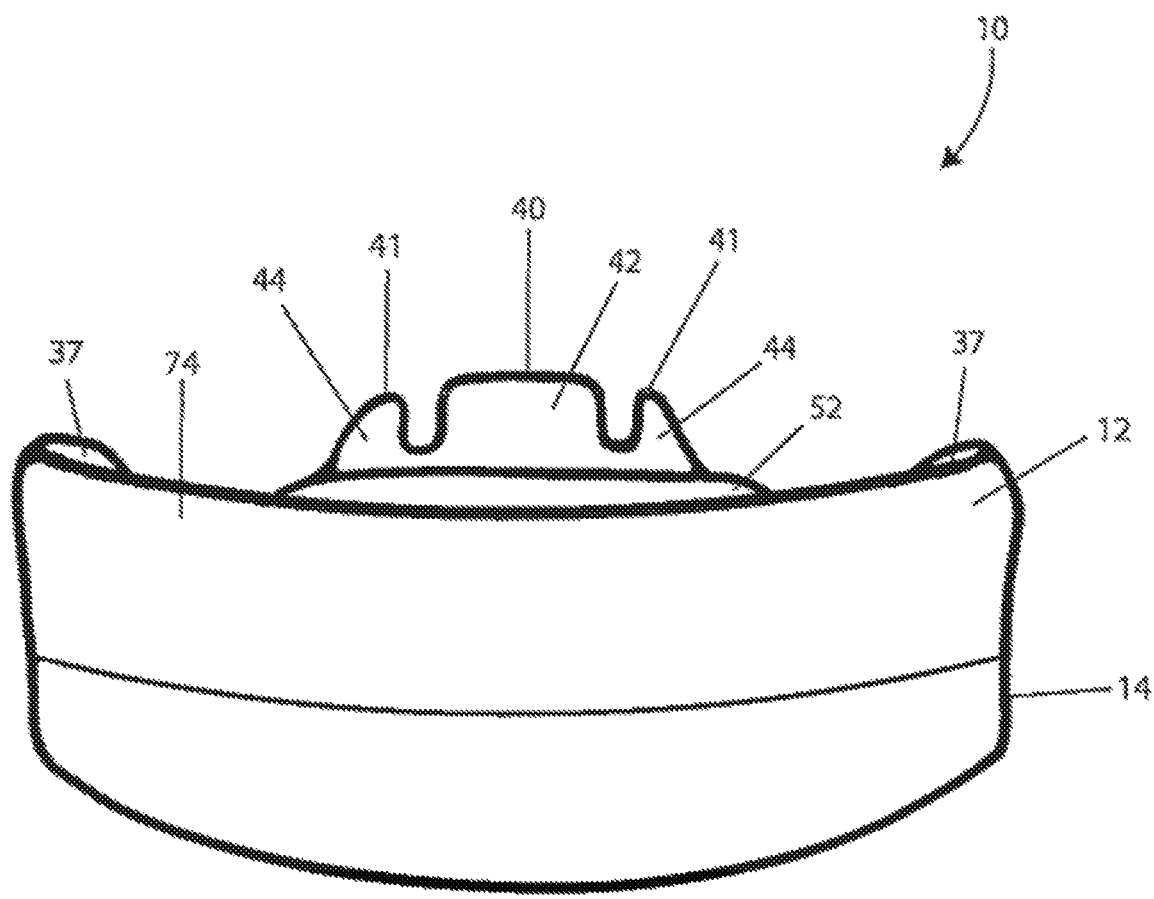
FIG. 10 illustrates a front view of an oral appliance in an embodiment of the present invention.
Figure 11:
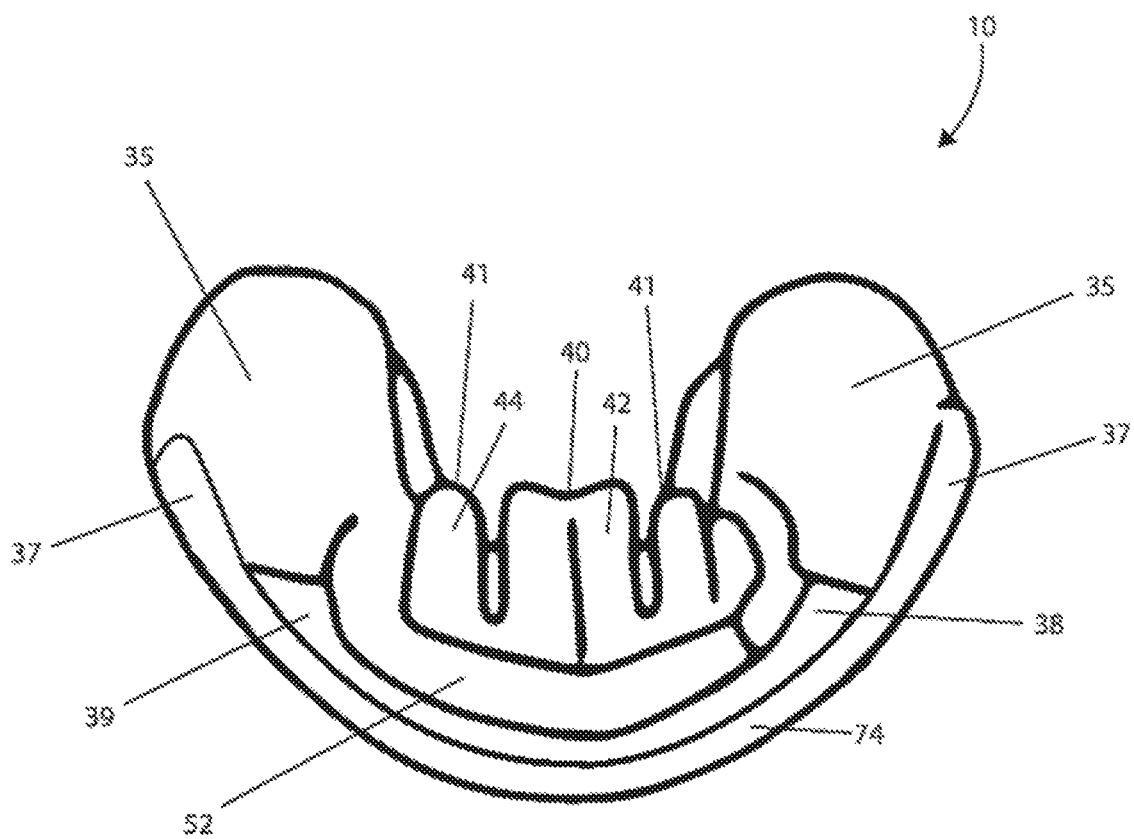
FIG. 11 illustrates a top view of an oral appliance in an embodiment of the present invention.
Figure 12:
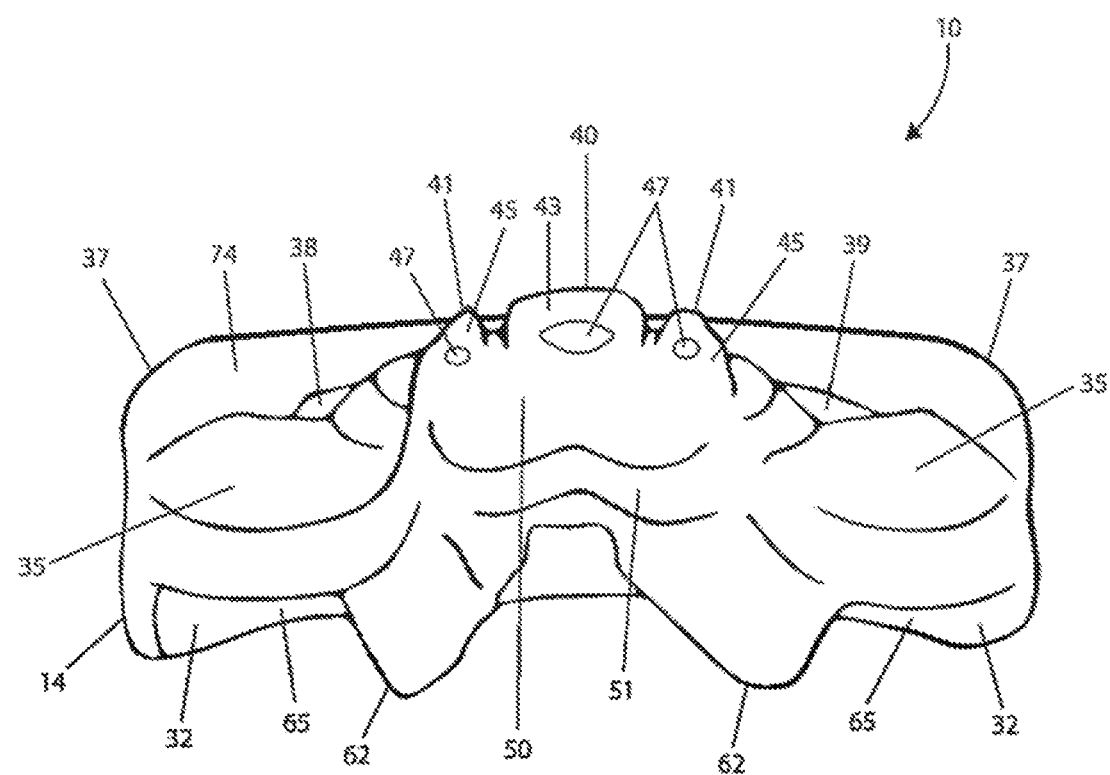
FIG. 12 illustrates a rear view of an oral appliance in an embodiment of the present invention.

In another embodiment illustrated in FIGS. 7 and 8, the upper body 12 of the appliance 10 may have an upper labial shield 70 arranged at an outer periphery of the upper body 12. The upper body may also have lateral palatal tabs 72 arranged at an inner periphery of the posterior portion 18 of the upper body 12. The upper labial shield 70 and the palatal tabs 72 may define an upper trough 75. The upper trough 75 may receive some and/or all of the upper dentition of the patient when the appliance 10 may be worn in the mouth of the patient. Depending on the shape and/or size of the appliance 10 with respect to the oral cavity and the upper dentition of the patient, some of the upper teeth may not fit within the upper trough 75.

As shown in FIGS. 7 and 8, the palatal tabs 72 may be formed on and/or may be attached at the inner periphery of the upper body 12 of the appliance 10. The palatal tabs 72 may be integrally formed with the appliance 10. The palatal tabs 72 of the appliance 10 may be adjacent to, may contact and/or may abut the palate of the patient.

The palatal tabs 72 may provide a surface against which the patient may exert pressure. For example, the patient may be instructed to elevate the palate by pushing the tongue against the palatal tabs 72. The tongue pressing against the palatal tabs 72 may exert lateral pressure that may widen a narrowed palate that may be caused, for example, by thumb sucking and/or finger sucking. The tongue pressing against the palatal tabs 72 may also inhibit and/or prevent narrowing of the palate with a continuing habit of thumb sucking. Further, the tongue pressing against the palatal tabs 72 may exert lateral pressure that may widen a narrowed palate in an instance in which advancement of the maxilla in a forward direction may not desired and/or indicated for the condition of the patient.

As shown, in an embodiment, the palatal tabs 72 may also have circular bumps 73 to remind the tongue where to push. The bumps 73 may be circular and/or spherical. It should be understood that the bumps 73 may be constructed in any shape as known by one having ordinary skill in the art.

Further, the bumps 73 on the palatal tabs 72 may remind the patient to move the tongue of the patient to the correct position during closure of the oral cavity and/or during wear of the appliance 10 in the closed position. Moreover, the palatal tabs 72 may encourage the patient to move the tongue of the patient to the correct position during the swallowing movements by the patient and/or during the resting periods between the swallowing movements by the patient.

In accordance with yet another embodiment as shown by FIGS. 9-12, the oral appliance 10 can include an upper labial shield 74 that is separated by several millimeters (e.g., from about 3 to about 4 mm) from the labial surface of the upper anterior teeth to aid in the elimination of mouth breathing, as well as to allow the anterior teeth and the maxilla to be advanced in a forward direction. In accordance with this specific embodiment, the shield 74 is positioned in the labial direction from the upper incisors by several millimeters, such that the separation would allow the upper arch to be advanced without being restricted by the upper shield since it does not contact the upper labial surface of the front teeth. Those of skill in the art should understand and appreciate herein that the labial shield 74 can be positioned high in the mouth to prevent any mouth breathing by the user, even if the jaw opens considerably at night.

Moreover, the present invention is not limited to the specific arrangement of the components illustrated in the figures. It should be understood that various changes and modifications to the presently preferred embodiments described herein will be apparent to those having ordinary skill in the art. Such changes and modifications may be made without departing from the spirit and scope of the present invention and without diminishing its attendant advantages. It is, therefore, intended that such changes and modifications be covered by the appended claims.

The invention claimed is:

1. A maxillary advancement appliance, the appliance comprising:
   a generally U-shaped upper body having an anterior portion configured to be adjacent to upper incisors and a posterior portion located rearward to the anterior portion, the upper body having an upper base with a perimeter defining an outer boundary and walls extending along the perimeter of the posterior portion of the upper body;
   a generally U-shaped lower body having an anterior portion configured to be adjacent to lower incisors, the lower body having a lower base with a perimeter defining an outer boundary, the lower base having a width which is configured to be greater than a width of the teeth of the user and wherein the lower body has walls extending along the perimeter of the lower body to define a trough, the trough being configured to contact the lower incisors as the appliance is worn in the mouth of the user;
   a tab comprising a center tab extending rearward from a center of the anterior portion of the upper body and two side tabs each at least partially separated from, but adjacent to a corresponding side of the center tab and extending rearward from the anterior portion of the upper body, the tab being configured to contact a maxilla when the appliance is worn within the mouth of the user to move the maxilla and upper teeth forward with respect to the mouth in response to pressure from a tongue;
   a shelf spaced from the tab and projecting generally rearward below the tab and configured to guide the tongue along the shelf into a palate of the user and
   palatal tabs extending from the walls on the posterior portion of the upper body, the palatal tabs being configured to receive pressure exerted by the tongue to encourage a widening of the palate.

2. The appliance of claim 1 further comprising:
   a raised surface on the posterior portion of the upper base of the upper body.

3. The appliance of claim 1 further wherein:
   the shelf is adjacent to the upper anterior base and configured to extend rearward in the mouth of the user.

4. The appliance of claim 1 further comprising:
   a ramp that extends from the upper base at an angle relative to the upper base on the anterior portion of the upper body, the ramp being configured to exert a force on the upper incisors and guide the upper incisors forward and downward as the appliance is worn within the mouth of the user.

5. The appliance of claim 1 wherein the upper base is configured to contact the furthest forward upper teeth within the mouth.

6. The appliance of claim 1 further comprising:
   a raised protrusion on the tab, the raised protrusion being configured to direct a tongue as the appliance is worn within the mouth of the user.

7. The appliance of claim 1 further comprising:
   a reline material exhibiting an adherence property that is configured to prevent the appliance from falling out of the mouth.

8. The appliance of claim 1 wherein the appliance is constructed from a resilient material.

9. The appliance of claim 1 wherein the trough has a roughened surface.

10. The appliance of claim 1 wherein the side tabs are configured to encourage the tongue to exert pressure against the side tabs to encourage a widening of the palate.

11. An orthodontic system worn adjacent to upper teeth and lower teeth in a mouth of a user, the orthodontic system comprising:
    an upper appliance having an anterior portion and a posterior portion located rearward of the anterior portion, the posterior portion being shaped to contact upper molars, and wherein the upper appliance has an inner perimeter and an outer perimeter, the outer perimeter being located exterior to the inner perimeter and posterior to anterior dentition;
    a lower appliance having an outer shield and inner ridges, the outer shield extending vertically downward from the lower appliance to define a trough in the lower appliance, and wherein the lower appliance is shaped to contact lower incisors and lower molars;
    a lining formed on at least a portion of at least one of the upper and lower appliance, the lining being configured to prevent the upper and lower appliance from falling out of the mouth;
    a ramp extending from the anterior portion of the upper appliance and configured to extend around the inner perimeter and to contact upper incisors to move the maxilla and upper anterior teeth in a forward direction, the ramp having a first anterior end and a first posterior end located rearward with respect to the first anterior end, and wherein the ramp extends rearward and diagonally from the inner perimeter of the upper appliance such that the first posterior end is positioned higher than the first anterior end;
    a tab extending at least partially from the ramp and having a second anterior end and a second posterior end located rearward with respect to the second anterior end, the tab extending rearward and diagonally from the first posterior end of, and to a position higher than, the ramp such that the second posterior end is positioned higher than the second anterior end, and wherein the tab is configured to contact the upper jaw of the user and apply a force to move the upper jaw forward relative to the lower jaw as the upper and lower appliance is worn within the mouth of the user; and
    palatal tabs extending from the posterior portion of the upper body, the palatal tabs being configured to receive pressure exerted by a tongue to encourage a widening of the palate;
    wherein the tab comprises a center tab extending rearward from a center portion of the ramp and two side tabs extending from corresponding sides of the ramp, each at least partially separated from, but adjacent to a corresponding side of the center tab and extending rearward from the anterior portion of the upper appliance.

12. The system of claim 11 further comprising:
    a shelf in the upper appliance, wherein the shelf forms a cavity with the tab behind the anterior portion of the upper appliance.

13. An appliance for correcting a malocclusion in a mouth of a user, the appliance comprising:
    a generally U-shaped upper body having an anterior portion and a posterior portion located rearward to the anterior portion, the upper body having an outer perimeter and an inner perimeter that is located interior to the outer perimeter;

a generally U-shaped lower body having an outer perimeter, the outer perimeter of the lower body having an anterior portion adjacent to lower incisors and a posterior portion located rearward to the anterior portion of the lower body, wherein the lower body has a lower labial shield extending along the outer perimeter of the lower body;

a tab extending generally upward from the anterior portion of the inner perimeter of the upper body, the tab being configured to contact a palate of the user as the appliance is worn within the mouth of the user;

the tab comprising a center tab extending rearward from a center of the anterior portion of the upper body and two side tabs, each at least partially separated from, but adjacent to a corresponding side of the center tab and extending rearward from the anterior portion of the upper body;

a shelf spaced from the tab and extending generally rearward from the anterior portion of the appliance, the shelf configured to guide a tongue of a user; and palatal tabs extending from the posterior portion of the upper body, the palatal tabs being configured to receive pressure exerted by the tongue to encourage a widening of the palate;

wherein, the shelf at least partially defines an area for the tongue in the lower body that is configured to make the appliance uncomfortable for a user to abnormally retain their tongue within the area.

\* \* \* \* \*